(12) United States Patent
Härer et al.

(10) Patent No.: US 8,045,774 B2
(45) Date of Patent: Oct. 25, 2011

(54) METHOD FOR CREATING MATERIAL-SELECTIVE VOLUME IMAGES

(75) Inventors: Wolfgang Härer, Erlangen (DE); Ernst-Peter Rührnschopf, Erlangen (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 658 days.

(21) Appl. No.: 12/283,418

(22) Filed: Sep. 11, 2008

(65) Prior Publication Data
US 2009/0086883 A1   Apr. 2, 2009

(30) Foreign Application Priority Data
Sep. 27, 2007   (DE) .................. 10 2007 046 359

(51) Int. Cl.
*G06K 9/00* (2006.01)
(52) U.S. Cl. .................. 382/128; 382/130; 382/173
(58) Field of Classification Search .................. None
See application file for complete search history.

(56) References Cited

U.S. PATENT DOCUMENTS
6,345,112 B1 *   2/2002   Summers et al. ............. 382/128

FOREIGN PATENT DOCUMENTS
WO      WO 2006/109233 A2   10/2006

OTHER PUBLICATIONS

Warp et al., "Quantitative evaluation of noise reduction strategie", Medical Physics, Feb. 2003, pp. 190-198, vol. 30, No. 2.
Alvarez et al., "Energy-selective Reconstructions in X-ray Computerized Tomography", Physical Medical Biology, 1976, pp. 733-744, vol. 21, No. 5.

* cited by examiner

*Primary Examiner* — Minh N Tang

(57) ABSTRACT

A method for creating material-selective volume images of various material components of an object to be examined is proposed. The method is based on multi-spectral projected images captured from various directions of projection, the images being captured using an X-ray machine, and makes it possible to quantitively exactly determine the material-selective volume images by way of iteration.

19 Claims, 6 Drawing Sheets

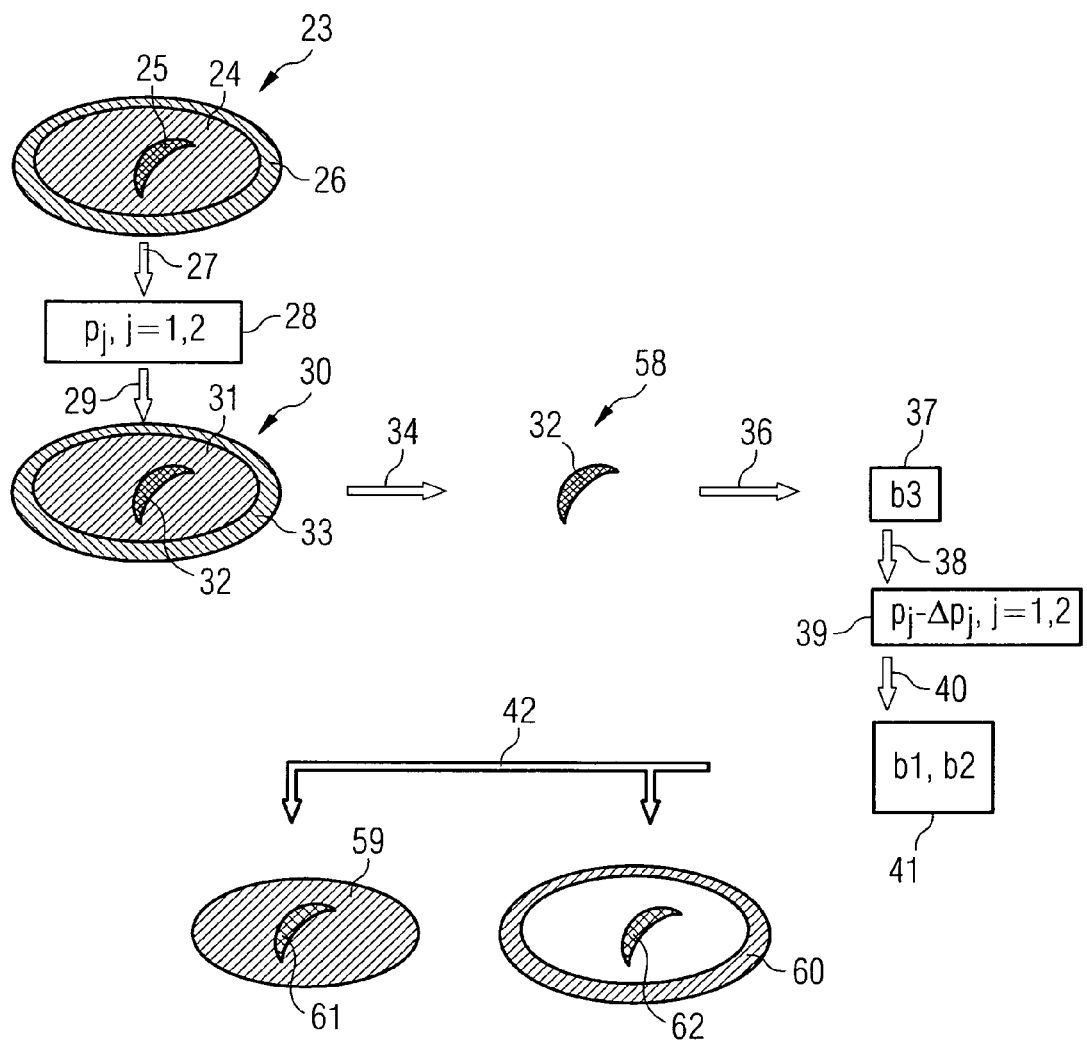

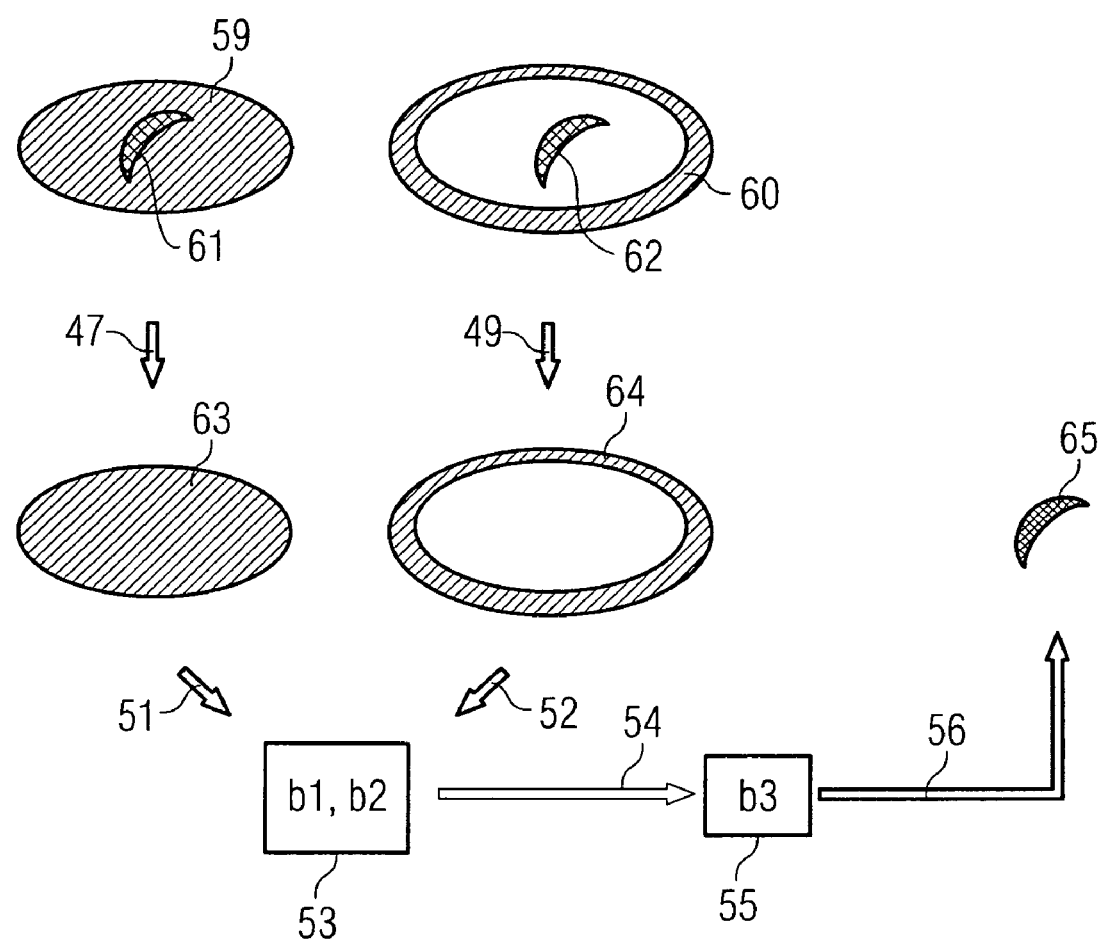

METHOD FOR CREATING MATERIAL-SELECTIVE VOLUME IMAGES

CROSS REFERENCE TO RELATED APPLICATIONS

This application claims priority of German application No. 10 2007 046 359.8 DE filed Sep. 27, 2007, which is incorporated by reference herein in its entirety.

FIELD OF INVENTION

The invention relates to a method for creating material-selective volume images comprising the method steps:
generating radiation in different energy fields using a radiation source;
x-raying an object, composed of various material components, in different energy fields and from different directions of projection;
loading a detector device with the radiation and capturing projected images in different energy fields by way of the detector device; and
creating material-selective volume images via an evaluation unit connected downstream of the detector.

BACKGROUND OF INVENTION

A method of this kind is known from ALVAREZ, R. B.; MACOVSKI, A.; "Energy selective reconstruction in X-ray computerized tomography", Phys. Med. Biol., vol. 21, pages 733-744, (1976). The known method is a computed tomography (CT) method in which projected images captured in different energy fields are used to create volume images of the three-dimensional density distribution of two different material components of an object to be examined. Volume images are in this case taken to mean three-dimensional images of the density distribution of different material components.

WARP, R. J.; DOBBINS, J. T.: "Quantitive evaluation of noise reduction strategies in dual-energy imaging", Med. Phys. 30 (2), February 2003 describes details of what is known as dual-energy projection imaging. In dual-energy projection imaging two projected images of the object to be examined are captured using two different X-ray spectra. By appropriate combination of the two projected images it is possible to separate radiologically different materials, for example soft tissue and bone. In particular it is basically possible to create mass occupancy images in which the mass occupancy of one material component respectively is displayed. For example purely bone images or soft tissue images can be created. Mass occupancy images are taken to mean two-dimensional images of the mass occupancy surface density in particular.

However, there are often more than two different materials in the beam path, for example soft tissue, calciferous tissue or bone or tissue filled with iodine as the contrast medium. Dual-energy projection imaging, in which just two different spectra are used, provides only two equations for two unknowns however. If two materials are to be separated therefore, the third material is incorrectly displayed as a combination of the other two. For this reason dual-energy projection imaging does not generally provide quantitively correct results in the case of more than two different materials.

The same applies to multi-spectral computed tomography in which material-selective volume images are created using multi-spectral projected images captured from different directions of projection.

SUMMARY OF INVENTION

An object of the invention is to disclose an improved method for multi-spectral computed tomography.

This object is achieved by a method with the features of the independent claims. Advantageous embodiments and developments are disclosed in the claims dependent thereon.

In the method a volume image of the object is first of all created using a series of projected images captured from different directions of projection. The volume image is then segmented into a number of main components, which corresponds to at most the number of energy fields, and at least one secondary component. Mass occupancy partial images linked to the at least one secondary component can be created in the different energy fields by subsequent back projection of the at least one secondary component in the different energy fields. In a further method step the mass occupancy partial images linked to the at least one secondary component are used to remove those fractions from the projected images created using the detector which are attributed to the at least one secondary component. Mass occupancy partial images of the main components can be created from the thus corrected projected images by inversion of a multi-dimensional attenuation function. These can in turn be used to create material-selective volume images of the main components.

Using this method the density distribution of a plurality of material components can be quantitively correctly reconstructed. The number of separated material components can be greater than the number of energy fields used for the shots. The creation of the material-selective volume images also implies correction of beam hardening. Therefore what is referred to as water correction or bone correction known from the prior art no longer needs to be carried out as well. Without additional correction of the beam hardening the reconstructed volume images do not contain any hardening effects therefore, such as an apparent reduction in the density toward the center of the image (=cupping) or band-like reductions in density between bones.

The material-selective volume image of the at least one secondary component can also be improved by segmenting the material-selective volume images of the main components into corrected volume images of the main components and the remnants of the at least one secondary component, and by creating corrected mass occupancy partial images of the main components by reprojection of the corrected volume images. A mass occupancy partial image of the at least one partial component can then be sought in the different energy fields, the mass occupancy partial image minimizing the difference in the projected images associated with the mass occupancy partial images of the main components and the secondary components in the different energy fields from the captured projected images. An improved material-selective volume image of the at least one secondary component can then be created from the mass occupancy partial image of the at least one secondary component.

The improved mass occupancy partial image of the at least one secondary component can in turn be used to improve the material-selective volume images of the main components by creating partial projected images linked to the at least one partial component in the different energy fields, and by removing fractions corresponding to the partial projected images, corrected projected images are produced in different energy fields from the captured projected images. Mass occupancy partial images of the main components can be created using the corrected projected images by inversion of a multi-dimensional attenuation function, it being possible to use the images in turn to create material-selective volume images of the main components.

The last two method steps mentioned, by which the material-selective volume images of the main component and the secondary component are improved, can be iteratively repeated until a quantity for the remnant of the at least one secondary component is undershot in the material-selective volume images of the main components or until the changes in the volume images in successive iteration steps fall below a predetermined quantity.

The captured projected images are preferably corrected by subtracting from the captured projected images partial projected images which are created using the attenuation function from the mass occupancy partial images of the at least one secondary component.

To keep the calculating effort for the application and inversion of the attenuation function low, pre-calculated tabular values that are stored in a memory are used for inversion of the attenuation function.

Pre-calculated tabular values that are stored in a memory can equally be used for reprojection of the volume images of the main component and the at least one secondary component.

Material components from the group comprising material components bone tissue, soft tissue, tissue enriched with contrast medium, and implants are preferably selected for the main components and secondary components. A separate three-dimensional illustration of a patient's body parts that are of interest from a medical perspective is thus possible.

BRIEF DESCRIPTION OF THE DRAWINGS

Further advantages and properties of the invention emerge from the following description in which exemplary embodiments of the invention are described in detail with reference to the drawings, in which:

FIG. 6 shows a drawing of a first method stage in which a material-selective volume image of soft tissue and a domed bone is created; and FIG. 7 shows a drawing of a second method stage, which follows the first method stage from FIG. 6, in which a material-selective volume image of a region of the body enriched with contrast medium is produced.

FIG. 1 shows a perspective view of an X-ray machine 1 which is suitable for multi-spectral X-ray imaging.

DETAILED DESCRIPTION OF INVENTION

Figure 1:
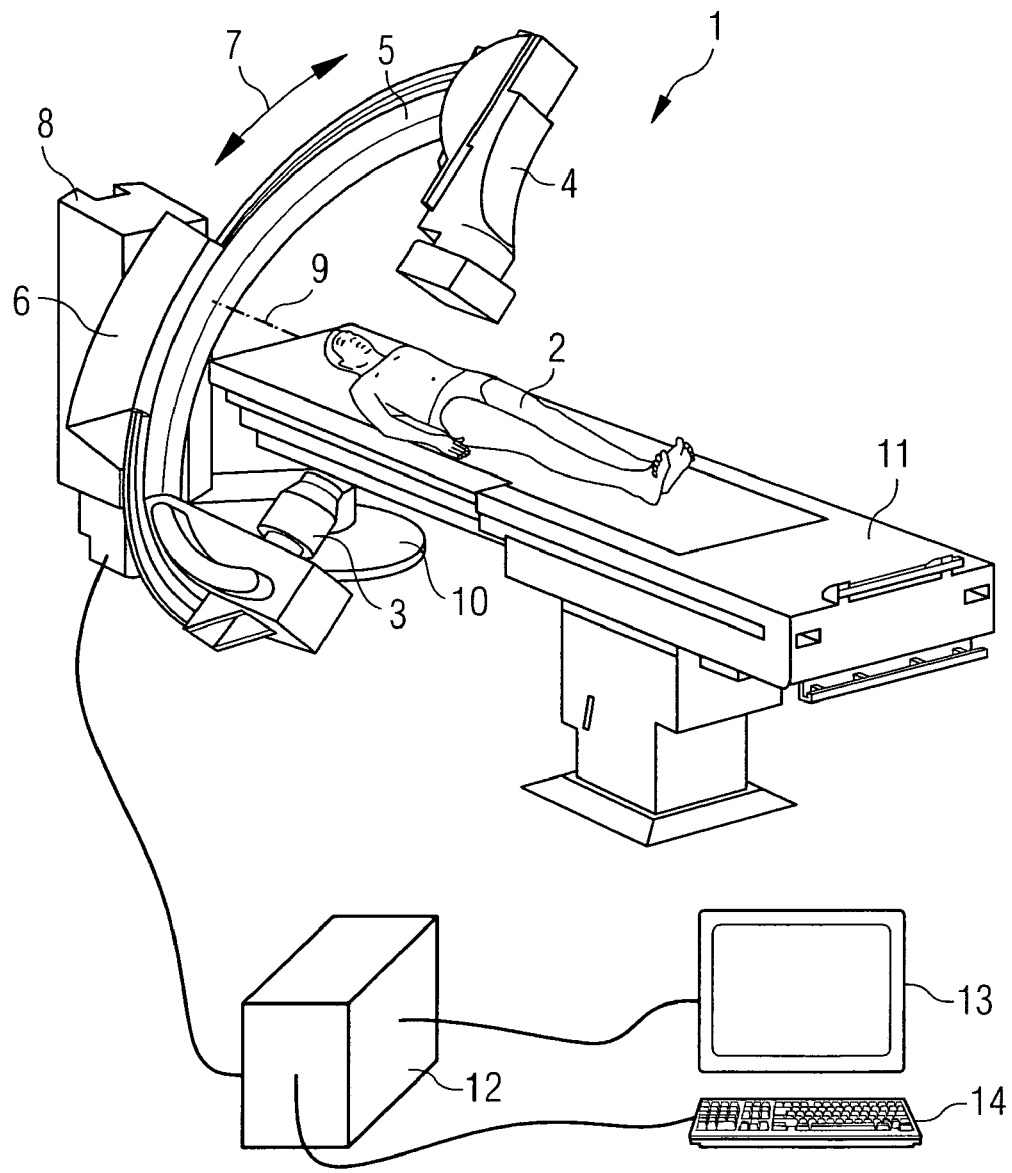
FIG. 1 shows an X-ray machine, comprising a C-arm, to the ends of which an X-ray tube and an X-ray detector are attached which are constructed for dual X-ray imaging.

In detail the X-ray machine 1 comprises an X-ray tube 3 and a detector 4 which captures the X-ray radiation emitted by the X-ray tube 3. The detector 4 is preferably a digital flat-panel detector. Nowadays flat-panel detectors of this kind with typical dimensions of about $20 \times 20$ cm$^2$ to $40 \times 40$ cm$^2$ are used. These flat-panel detectors comprise photo diodes of amorphic silicon. There are no restrictions in relation to size and materials used. By using a flat-panel detector of this kind the X-ray machine 1 can be used in an intervention for multi-spectral three-dimensional imaging as well as for two-dimensional radioscopy. The X-ray machine is also suitable for angiography in which vessels are examined with the aid of contrast medium.

En route to the detector 4 the X-ray radiation passes through the patient 2, so the detector 4 captures projected images of the patient 2. Since the X-ray radiation is partially attenuated in the body of the patient 2 by scattering or absorption, the projected images reproduce the attenuation of the X-ray radiation through the patient 2.

The X-ray tubes 3 and the detector 4 are attached to the ends of a C-arm 5 which is held by a bracket 6. The C-arm 5 is mounted in the bracket 6 so as to move in a circumferential direction 7. The bracket 6 is in turn attached to a stand 8 so as to be pivotal about an axis of rotation 9. The stand 8 sits on a base 10 which allows the stand 8 to move on the ground.

During operation of the X-ray machine 1 the C-arm 5 typically executes a swiveling movement about the axis of rotation 9 and in the process moves around a patient's couch 11 on which the patient 2 is supported. In addition to a swiveling movement the C-arm 5 can also execute significantly more complex movements which include a movement in the circumferential direction 7 or movement of the stand 8.

While the C-arm 5 is moving projected images are captured in different energy fields. For example a plurality of projected images can be captured in different energy fields for each direction of projection, in which fields the radiation that has passed through the patient 2 has different energy distributions. The projected images captured in different energy fields can also be captured at different angles of projection respectively. In this case the projected images captured in different energy fields can potentially be made to coincide with respect to the angle of projection by interpolation and subsequent registering. The energy field of the X-ray radiation used for capturing the projected images can be changed for example by varying the X-ray voltage of the X-ray tubes 3. Spectral X-ray filters can also be used. Finally X-ray images can also be captured in different energy fields if an energy-selective detector is used for the detector 4.

The projected images are supplied to an evaluation unit 12 which is connected downstream of the detector 4. The evaluation unit 12 creates material-selective volume images of the body parts from the projected images captured in different energy fields. These volume images can be displayed on a monitor 13 connected to the evaluation unit 12. Input devices 14, with which the X-ray machine 1 can be controlled, are also connected to the evaluation unit 12. The monitor 13 can also be located directly above the patient's couch 11 while the input devices 14 are arranged in the region of the patient's couch 11, so the user can control the movement of the C-arm 5 and can monitor the internal structure of the body of the patient 2.

The conventional methods for creating material-selective volume images do not lead to a quantitively exact separation of the individual material components in volume images. Also, when using two different spectra, only two body parts can be separated. A method is therefore described hereinafter which allows quantitively exact material-selective volume images to be created for more than two body parts.

It should be noted that the method described hereinafter can be used not only for X-ray machines with C-arms but also for X-ray machines in which the X-ray tubes and the X-ray detector revolve around the patient in a fixed portal, or for X-ray machines in which the patient is X-rayed in different directions of a projection using a fixed detector.

1. Basic Requirements

It must be assumed that the projection measuring data—apart from noise—are error-free. In this respect interference must be eliminated by calibration and corrections. Metrological or calculational measures are required in particular especially in the case of CT with a flat-panel detector. Suitable correction methods are described for example in ZELLERHOFF, M.; SCHOLZ, B.; RÜHRNSCHOPF, E.-P.; BRUNNER, T.: "Low contrast 3D reconstruction from C-arm data"., Proceedings of SPIE. Medical Imaging 2005, vol. 5745, pages 646-655 and in the publication KYRIAKOU, Y.; RIEDEL, T.; KALENDER; W. A.: "Combining deterministic and Monte Carlo calculations for fast estimation of scatter intensities in CT", Phys. Med. Biol. 51 (2006) pages 4567-4586.

Figure 2:
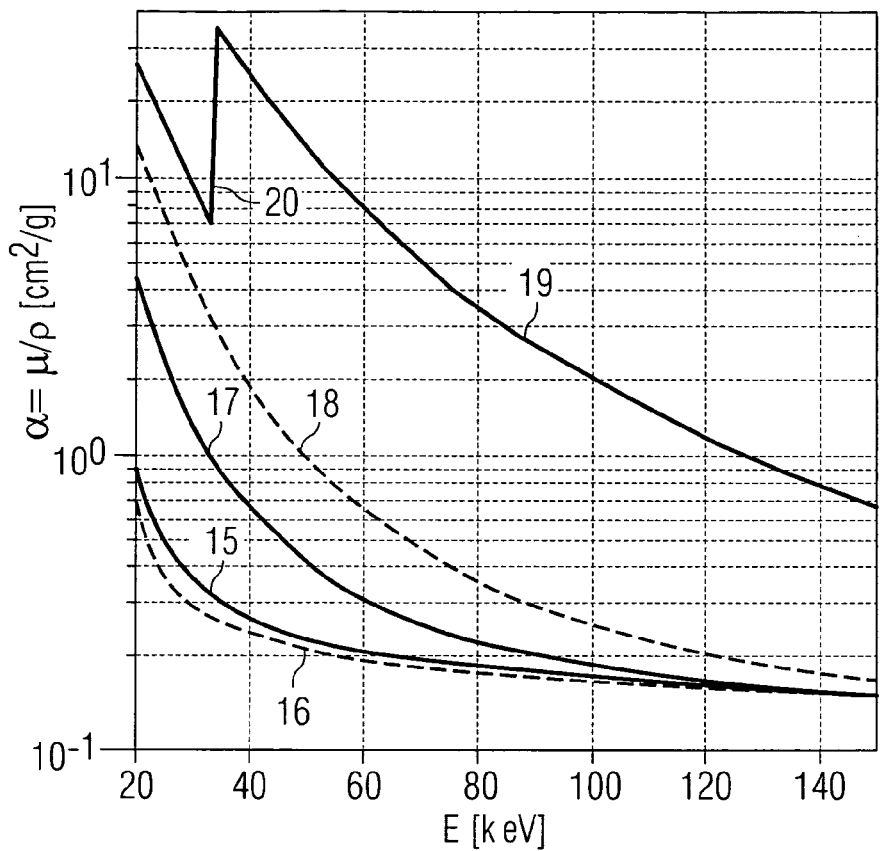
FIG. 2 shows the characteristic of the mass attenuation coefficient as a function of the photon energy for various body parts.

For the problem being considered it is also assumed that the object or the volume range of a patient that is to be imaged comprises at least three radiologically different materials. Radiologically different materials are taken to mean those materials of which the attenuation coefficients have a different energy dependency and which cannot be converted one in the other by a proportionality constant. FIG. 2 shows examples.

FIG. 2 shows the dependency of the mass attenuation coefficient for water $(\mu/\rho)$ (E) of the photon energy E. A mass attenuation curve 15 for water is substantially congruent with a mass attenuation curve for blood although blood has a greater density $\rho$ than water. Fatty tissue on the other hand has a mass attenuation curve 16 that differs slightly from the mass attenuation curve 15. A further mass attenuation curve 17 indicates the characteristic of the mass attenuation coefficient of bone tissue. Further mass attenuation curves 18 and 19 describe the characteristic of the mass attenuation coefficients of calcium and iodine which has a K edge 20 in the case of photon energy of 33.2 keV. Iodine is often used as a contrast medium.

With reference to FIG. 2 it is clear that bone tissue absorbs X-ray radiation more strongly than soft tissue. However the attenuation coefficient of X-ray radiation decreases more strongly at higher energies in the case of bone tissue than the absorption of soft tissue. The energy dependency of the mass attenuation curve 15 for water and of the mass attenuation curve 16 for fatty tissue is also slightly different. The materials shown here should therefore be regarded as radiologically different on the basis of the different attenuation properties.

It is also assumed that at least one material in the volume range may be identified by anatomical, geometric or other criteria and can be separated by segmenting for instance.

1. Basic Concept (Linearized Simplification)

First of all the basic concept shall be illustrated by way of a simplified linear model.

By way of example three different materials are present in the beam path, namely soft tissue, bone and iodine. In the simplified linearized model, which would apply for two monochromatic radiation sources with different energy, the amounts of the individual materials in the beam path add up linearly to the total logarithmically standardized CT projection value. For the energy j the amount of material k would be the product of mass occupancy $b_k[g/cm^2]$ and mass attenuation coefficient $\alpha_{jk}[cm^2/g]$:

$$\alpha_{jk} b_k \quad (\#1.0)$$

For the sake of simplicity the mass occupancy surface density will hereinafter be called mass occupancy for short. Since the mass occupancy is equal to the line integral of a density distribution, with constant density the mass occupancy can readily be converted into the material thickness.

It should also be noted that in the case of known density, the mass attenuation coefficients $\alpha_1(E)=(\mu_1/\rho_1)(E)$, $\alpha_2(E)=(\mu_2/\rho_2)(E)$ and $\alpha_3(E)=(\mu_3/\rho_3)(E)[cm^2/g]$ can be converted into what are referred to as the linear attenuation coefficients $\mu_1$, $\mu_2$ and $\mu_3$. With known densities $\rho_1, \rho_2, \rho_3$ the mass occupancies $b_1, b_2, b_3 [g/cm^2]$ can be converted into the material thicknesses $x_1, x_2$ and $x_3$ [cm].

The following then applies for three materials in the beam path:

$$p_1=f_1(b_1,b_2,b_3)=\alpha_{11}b_1+\alpha_{12}b_2+\alpha_{13}b_3$$

$$p_2=f_2(b_1,b_2,b_3)=\alpha_{21}b_1+\alpha_{22}b_2+\alpha_{23}b_3 \quad (\#1a,b)$$

These two equations are not sufficient to conclusively calculate the three unknowns $b_1, b_2, b_3$.

The equations (#1a, b) apply to the individual measuring beam which should be associated with a direction of projection and an individual pixel on the detector. CT projection values $p_j$ are therefore a function of the detector coordinates (x, y) and of the angle of projection phi respectively. The volume image $q_j$ of an object may be reconstructed by means of CT reconstruction from all of the data $p_j(x,y,phi)$. A volume image is in this case taken to mean the three-dimensional distribution of the linear attenuation coefficient or the density. This applies generally to each of the two chosen energies or spectra.

The basic concept for a quantitively correct reconstruction is as follows, where as a thought experiment we would like to examine the elimination of a third material, for example bone:

We can assume that within the reconstructed volume the contours and the regions of different materials, such as soft tissue or bone, can be well distinguished and can be separated by segmenting algorithms.

Following segmenting and reprojection for each measuring beam the wavelengths and the products of wavelengths*linear attenuation coefficient or mass occupancy*mass attenuation coefficient can therefore be determined for the third material. Reprojection is in this case taken to mean the calculated simulation of the penetration and attenuation of each measuring beam through the object. An algorithm that is suitable for this purpose is disclosed for example in MUELLER, K.; YAGEL, R.; WHELLER, J. J.: "A Fast and Accurate Projection Algorithm for 3D Cone-Beam Reconstruction with Algebraic Reconstruction Technique (ART)", presented at the SPIE Medical Imaging Conference, San Diego, February 1998. A further reprojection algorithm of this kind is disclosed in SIDDON, R. L.: "Fast calculation of the exact radiological path for a three-dimensional CT array". Med. Phys.,12 (2), pages 252-255, March/April 1985.

We will call the fractions obtained with the reprojection algorithm:

$$\Delta p_j^{(3)} \quad (\#2.0)$$

This results in the possibility of eliminating the third term in equations (#1a, b) which contains the value of the third material relating to the projection value. The system of equations, which originally comprised two equations for three unknowns (water, iodine, bone), thereby becomes a solvable system of equations of two equations for two unknowns (water, iodine):

$$f'_1(b_1,b_2)=p_1-\Delta p_1^{(3)}=f_1(b_1,b_2,b_3)-\Delta p_1^{(3)}\approx\alpha_{11}b_1+\alpha_{12}b_2 \quad (\#2a,b)$$

$$f'_2(b_1,b_2)=p_2-\Delta p_2^{(3)}=f_2(b_1,b_2,b_3)-\Delta p_2^{(3)}\approx\alpha_{21}b_1+\alpha_{22}b_2$$

The $\approx$ symbol is intended to indicate that extraction of the bone fractions (#2.0) is generally not quite exact.

Assuming that the effective attenuation coefficients for water and iodine are in principle known, the material thicknesses $b_1$ and $b_2$ of the two materials can be calculated for each measured value. From this two volume images are obtained, by way of example by CT reconstruction, for the density distribution of the two first materials (water and iodine).

2. More Precise Non-Linear Theory

The basic concept described in section 1 will now be transferred hereinafter to the case of polychromatic radiation.

2.1 Non-Linear Formulation

In reality X-ray tubes provide polychromatic spectra and instead of the simple linear equations (#2a, b) the non-linear relationships (#3a, b) given hereinafter then applies.

In theory the following applies for the CT projection values (=logarithmized primary attenuations) with the effective spectra $W_1(E)$ and $W_2(E)$ in the case of three different materials with mass attenuation coefficients $\alpha_1(E)$, $\alpha_2(E)$, $\alpha_3(E)$ [cm$^2$/g] as a function of the mass occupancies $b_1$, $b_2$, $b_3$ [g/cm$^2$], which the X-ray beam penetrates:

$$p_1 = M_1(b_1,b_2,b_3) = -\ln(\int e^{-\alpha_1(E)b_1 - \alpha_2(E)b_2 - \alpha_3(E)b_3} W_1(E) dE) \quad (\#3a),$$

$$p_2 = M_2(b_1,b_2,b_3) = -\ln(\int e^{-\alpha_1(E)b_1 - \alpha_2(E)b_2 - \alpha_3(E)b_3} W_2(E) dE) \quad (\#3b),$$

in vector form:

$$M(b_1, b_2, b_3) = \begin{bmatrix} M_1(b_1, b_2, b_3) \\ M_2(b_1, b_2, b_3) \end{bmatrix}. \quad (\#3)$$

It should be noted that the effective spectra W1(E) and W2(E) already include the effect of radiation filters and the energy-dependent detector sensitivity.

Figure 3:
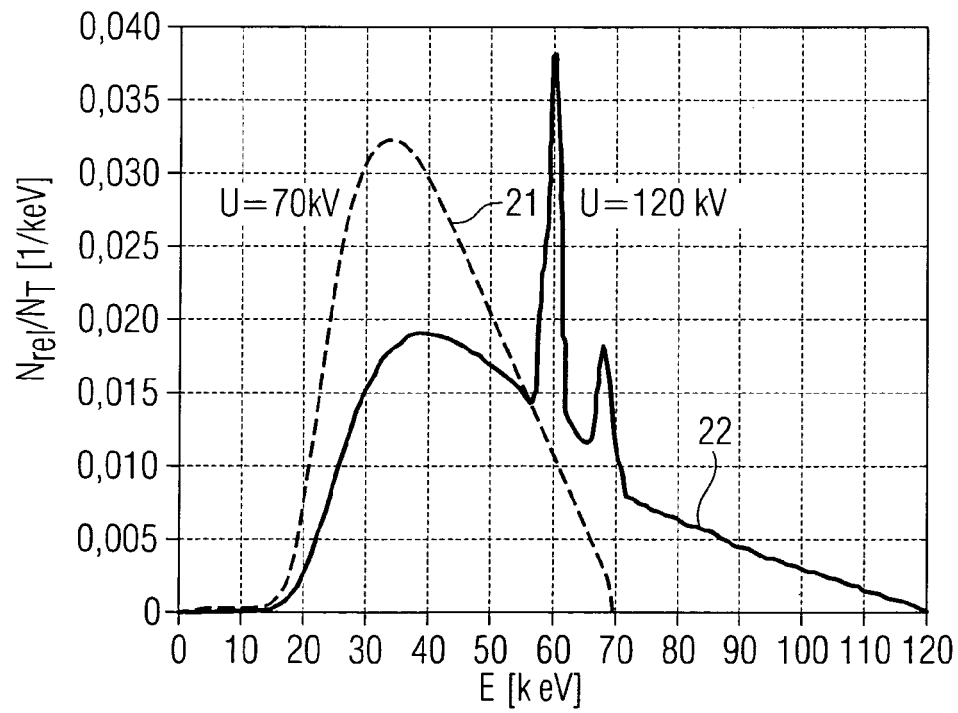
FIG. 3 shows two photon spectra, captured at different X-ray voltages, of an X-ray tube with a tungsten anode.

FIG. 3 shows examples of two effective spectral distributions $W_1(E)$ and $W_2(E)$ which correspond to the tube voltages 60 kV and 120 kV. In FIG. 3 the relative photon frequency $N_{ref}/N_T$ per 1 keV interval is plotted against the photon energy E in keV, where $N_T$ is the total number of photons in the respective spectrum. An X-ray spectrum 21 is associated in this case with a tube voltage of 70 kV and an X-ray spectrum 22 with a tube voltage of 120 kV.

2.2 Reduction to Two-Dimensional Vector Mapping

The following considerations logically apply to each of the two spectra:

We are assuming that the mass occupancy of the third material $b_3$ is known from segmenting and reprojection. The projection value fraction of the third material is then given by:

$$\Delta p_j = g(b_3) = -\ln(\int e^{-\alpha_3(E)b_3} W_j(E) dE), j=1,2 \quad (\#4).$$

If this fraction is subtracted from equation (#3a, b) the total projection value fraction $M_j$, which is based on the first and second materials, is then obtained:

$$M_j^\#(b_1, b_2 \mid b_3) = p_j - \Delta p_j \quad (\#5)$$
$$= M_j(b_1, b_2, b_3) - g_j(b_3)$$
$$= -\ln\left(\int e^{-\alpha_1(E)b_1 - \alpha_2(E)b_2 - \alpha_3(E)b_3} W_j(E) dE\right) +$$
$$\ln\left(\int e^{-\alpha_3(E)b_3} W_j(E) dE\right)$$

$$= -\ln\left(\frac{\int e^{-\alpha_1(E)b_1 - \alpha_2(E)b_2 - \alpha_3(E)b_3} W_j(E) dE}{\int e^{-\alpha_3(E)b_3} W_j(E) dE}\right)$$

$$= -\ln\left(\int e^{-\alpha_1(E)b_1 - \alpha_2(E)b_2} \overline{W_j^{(b_3)}}(E) dE\right)$$

the hardened spectrum pre-filtered by the third material with mass occupancy $b_3$ having been defined by $$\overline{W_j^{(b_3)}}(E) = \frac{e^{-\alpha_3(E)b_3} W_j(E)}{\int e^{-\alpha_3(E)b_3} W_j(E) dE} \quad (\#6)$$

The non-linear system of equations (#7a, b) of two equations with two variables $b_1$, $b_2$ and a parameter $b_3$ accordingly takes the place of the non-linear system of equations (#3a, b) of two equations with three variables:

$$M_1^\#(b_1, b_2 \mid b_3) = -\ln(\int e^{-\alpha_1(E)b_1 - \alpha_2(E)b_2} \overline{W_1^{(b_3)}}(E) dE) \quad (\#7a)$$

$$M_2^\#(b_1, b_2 \mid b_3) = -\ln(\int e^{-\alpha_1(E)b_1 - \alpha_2(E)b_2} \overline{W_2^{(b_3)}}(E) dE) \quad (\#7b)$$

The two functions defined in equations (#7a, b) can be calculated in advance for all pairs of mass occupancies $b_1$, $b_2$ and for various parameter values of mass occupancies $b_3$ of the third material since the energy-dependent mass attenuation coefficients are known and the spectra can also be assumed to be known.

In compact vector notation where $\underline{b}=(b_1, b_2)$ we write $$\underline{M_{(b_3)}}(\underline{b}) = \begin{bmatrix} M_1^\#(b_1, b_2 \mid b_3) \\ M_2^\#(b_1, b_2 \mid b_3) \end{bmatrix} \quad (\#8)$$

The 2×2 vector function, defined by (#8) and (#7), of two function values with two variables can be inverted for each fixed parameter value $b_3$, for example using the Newton method for vector functions which is described in PRESS, FLANNERY, TEUKOLSKY, VETTERLING: "Numerical Recipes. The Art of Scientific Programming", Cambridge University Press, 1989. We designate the inverse 2×2 vector function:

$$\underline{G_{(b_3)}} = \underline{M_{(b_3)}}^{-1} \quad (\#9)$$

The result of inversion is a family (with family parameter $b_3$) of 2×2-dimensional tables which clearly allocate each pair of projection value differences (to be interpreted according to the definition in equation (#5)) a pair ($b_1$, $b_2$) of mass occupancies of the first material and the second material.

2.3 Special Case for Reduction to One-Dimensional Equation

In section 4.2.1 the one-dimensional vector function is required within the framework of an iterative method and this is determined by retaining the parameters ($b_1$, $b_2$) in equation (#3):

$$M_{(b_1,b_2)}(b_3) = M(b_1, b_2, b_3) \quad (\#10),$$

and the scalar function which describes the discrepancy in the form of the mean quadratic difference between calculated and measured projected values:

$$H(b_3) = H_{(b_1,b_2)}(b_3) = \|M_{(b_1,b_2)}(b_3) - p\|^2 \quad (\#11).$$

In (#11) the projection value pair ($p_1$,$p_2$) for the two spectra has been described as the vector p.

Section 4.2.1 proposes definition of $b_3$ by a local solution of the minimization problem $$\hat{b_3} = \min_{b_3} H(b_3) \qquad (\#12)$$

The minimum can be calculated using numerical standard algorithms, such as the bisection method. Such methods are described for example in PRESS, FLANNERY, TEUKOLSKY, VETTERLING: "Numerical Recipes. The Art of Scientific Programming", Cambridge University Press, 1989.

3. Assumed Procedures

The method we propose assumes the presence of six procedures:

Procedure 1:

A CT image reconstruction algorithm B is required for creating volume images. Reference is made to the fact that negative image values are also allowed within the framework of CT image reconstruction algorithm B.

Procedure 2:

Segmenting S is preferably carried out with the aid of threshold criteria.

Procedure 3:

A reprojection algorithm R is required to produce projected images from the volume images.

Procedure 4:

The fourth required procedure is the multi-dimensional function M by which the non-linear (logarithmized) attenuation is linked as a function of the two spectra used for dual-energy imaging to the mass occupancies of three materials, of which the energy-dependent attenuation coefficients are known. The physical connection is established by equations (#3a, b) or by tables which have been calculated on the basis of these formulae;

Procedure 5:

The inverse vector function $G(_{b_3})$ according to equation (#9) is required as the fifth procedure. This procedure can be pre-calculated as an additional multi-dimensional family of tables;

Procedure 6:

Finally a procedure for solving equations (#11-12) is required. As already mentioned this procedure can be implemented with standard algorithms.

4. Multi-Stage Problem-Solving Method

The individual steps of a multi-stage problem-solving method are described hereinafter. This involves a plurality of gradual refinement stages, each stage being divided into a plurality of individual steps.

4.1 Stage 0: the Basic Method

The basic method described hereinafter provides the solution even if the third material has the homogeneity property of constant density. In the general case of inhomogeneous density distribution an approximate solution is obtained which can be used as the start of a subsequent iterative method which is described in section 4.2. The basic method is schematically illustrated for two examples in FIGS. 4 and 6 and will be described in more detail hereinafter with reference to FIGS. 4 and 6.

Step 1:

Image reconstruction B from projection data. In principle the reconstruction of one data record for one spectrum is sufficient. The minimal-noise linear combination of the two data records described in the publication ALVAREZ, R.; SEPPI, E.: "A comparison of noise and dose in conventional and energy selective computed tomography". IEEE Trans. Nucl. Sci., April 1979, 2853-2856 is particularly advantageous however.

Step 2:

Segmenting S of the reconstructed volume, so only two different materials are then found in one volume segment and the other volume segment then contains only the third material.

Step 3:

(Simplified) reprojection R of the volume consisting solely of the third material: the simplification lies in the fact that firstly a constant density and a constant linear attenuation coefficient must be assumed in the volume segment of the third material. An estimate of the mean mass occupancy of the third material: $b_3^{(0)}$ is then produced for each measured value Step 4:

The projection fractions of the third material are obtained from $b_3^{(0)}$ by means of equation (#4):

$$\Delta p_j^{(0)} = g_j(b_3^{(0)}) \qquad (\#13)$$

Step 5:

Forming the projection differences, which are to be associated with the first material and the second material, according to the right-hand side of the first line of equation (#5).

Step 6:

Inversion by means of table (#9) for parameter value $b_3$. The result is pairs of mass occupancies $b_1$ and $b_2$ for each pixel and each direction of projection.

Step 7:

Each mass occupancy, in particular $b_1$ or $b_2$ [g/cm$^2$], can be interpreted as a line integral of a density distribution [g/cm$^3$] of the first and second materials. Therefore $b_1=b_1(x,y,phi)$ and $b_2=b_2(x,y,phi)$ are CT projection data records for each pixel and each direction of projection. CT image reconstructions from $b_1$ and $b_2$ provide reconstructed volume renderings of the three-dimensional density distributions $q_1$, $q_2$ of materials 1 and 2:

$$B(b_1)=q_1 \qquad (\#14a)$$

$$B(b_2)=q_2 \qquad (\#14b)$$

4.2 Iterative Improvements

The results may be improved using an additional iterative cycle. This is primarily expedient if, for example, following the CT image reconstructions according to step 7 in the previous section, there are still residual fractions (not equal to 0) in $q_1$, $q_2$ in which volume ranges identified with the third material occur which have been previously eliminated during segmenting (step 2).

Segmenting of volume ranges identified with the third material is hereinafter designated $S_3$.

The intermediate results or even end results of the basic method in section 4.1 are used as initial values for a subsequent iterative cycle. These initial values from steps 3, 4, 6 and 7 are provided with a superscript (0) for identification, i.e.:

$$b_3^{(0)},b_1^{(0)},b_2^{(0)},q_1^{(0)},q_2^{(0)}$$

4.2.1 First Iterative Partial Cycle ($b_3$—Improvement)

Figure 5:
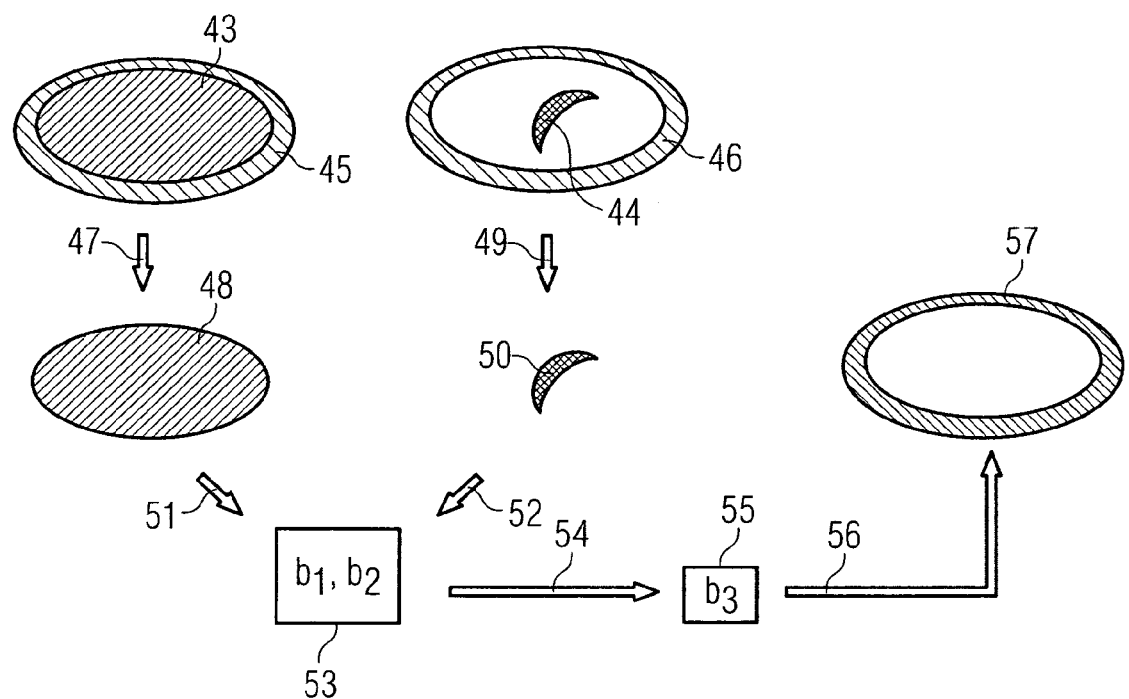
FIG. 5 shows a drawing of a second method stage, which follows the first method stage from FIG. 4, in which a material-selective volume image of a domed bone is produced.

FIG. 5 and FIG. 7 show the individual processing steps for two examples.

Step 1:

Segmenting out the remnant (residue) of the volume images $q_1^{(0)}$, $q_2^{(0)}$ that incorrectly appear in the range of the third material $$S_3(q_1^{(0)}) \qquad (\#15a)$$

$$S_3(q_2^{(0)}) \qquad (\#15b)$$

Step 2:
Elimination of the remnants from volume images $q_1^{(0)}$, $q_2^{(0)}$:

$$q_1^{(1)} = q_1^{(0)} - S_3(q_1^{(0)}) \quad (\#16a)$$

$$q_2^{(1)} = q_2^{(0)} - S_3(q_2^{(0)}) \quad (\#16b)$$

Step 3:
Reprojection of the corrected volume images $$b_1^{(1)} = R(q_1^{(0)}) \quad (\#17a)$$

$$b_2^{(1)} = R(q_2^{(0)}) \quad (\#17b)$$

Step 4:
Determining the mass occupancy of the third material by solving equation (#12) by using $b_1^{(1)}$, $b_2^{(1)}$.

$$b_3^{(1)} \quad (\#18)$$

Step 5:
New CT reconstruction of the density distribution of the third material $$q_3 = B(b_3^{(1)}) \quad (\#19a);$$

Step 6:
Checking the termination condition: the method can be terminated if the reconstructed density distribution of the third material does not parasitically scatter into the ranges of the first and second materials:

$$q_3^{(1)} = q_3^* \quad (\#19b).$$

Otherwise the parasitic regions are eliminated by segmenting again:

$$q_3^{(1)} = S_3(q_3^*) \quad (\#20).$$

4.2.2 Second Iterative Partial Cycle ($b_1$, $b_2$—Improvement)

The cycle can now be terminated or to further improve the density reconstruction of the first material and second material can be followed up with an additional iterative cycle which substantially comprises steps 3 to 7 of the basic method in section 4.1. The only fundamental difference lies in the fact that the simplifying assumptions for reprojection in step 3 of the basic method may be omitted since $q_3^{(1)}$ is already a generally inhomogeneous density distribution. The result will then be improved density reconstructions $q_1^{(2)}$, $q_2^{(2)}$, corresponding to the equations (#14a) and (#14b).

If the entire succession of steps up to this point is considered then it can be seen that what is involved is a sequence of two cycles—the composition of these two partial cycles is called a long iterative cycle.

As a rule the method will be terminated after one or a few long iterative cycle(s).

5. Variants and Generalizations 5.1 Exemplary Embodiments

Figure 4:
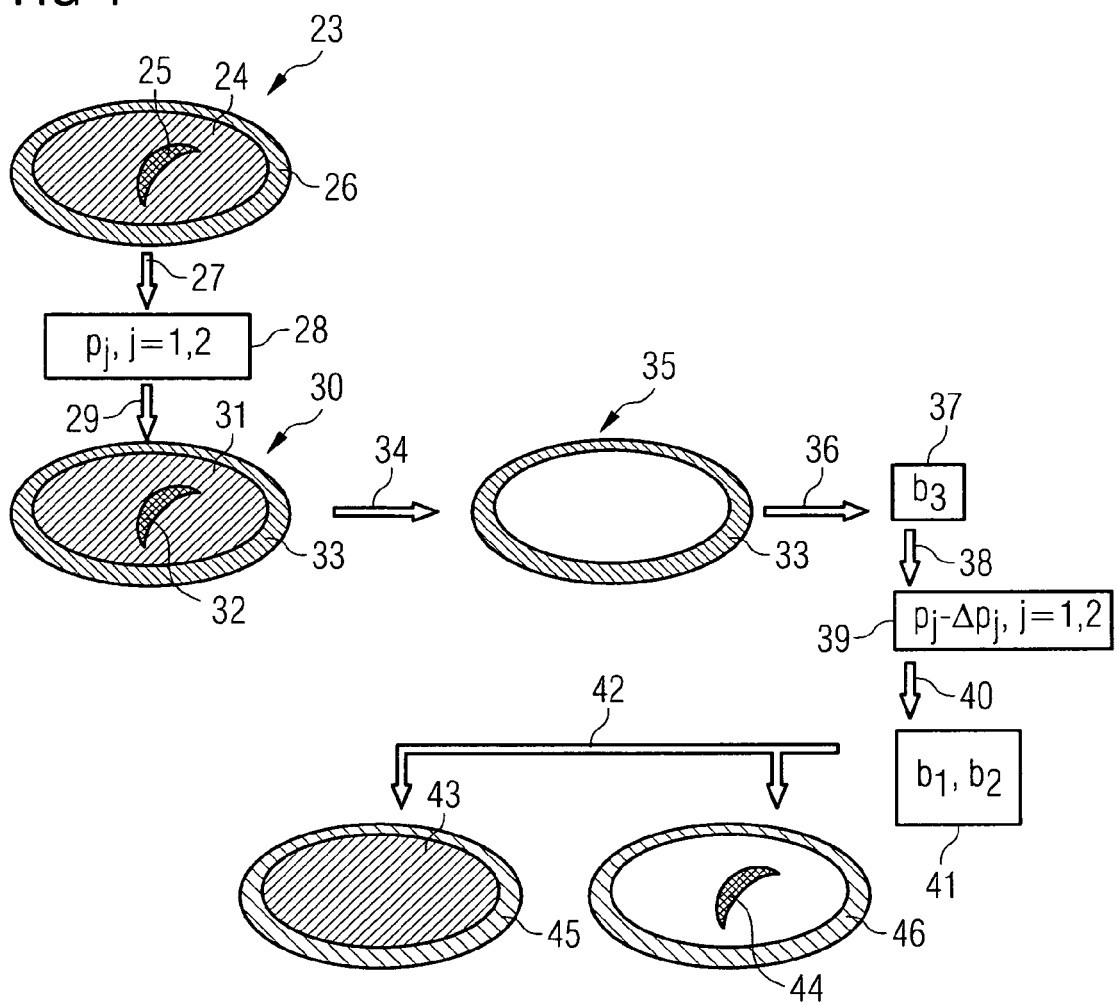
FIG. 4 shows a drawing of a first method stage in which a material-selective volume image of soft tissue and of a body region enriched with contrast medium is created.

FIGS. 4 and 5 illustrate the procedure for the case where the first material of a body region 23 of the patient 2 that is being examined is soft tissue 24, the second material is a contrast medium-filled vessel 25 and the third material is a dome-shaped bone 26 surrounding the soft tissue 24 and the vessel 25. This kind of body region 23 occurs for example in the region of the skull or chest of the patient 2.

The method steps shown in FIG. 4 correspond to the steps 1 to 7 described in section 4.1. Projected images 28 of the body region 23 are firstly created by X-ray imaging 27. A volume image 30 is created therefrom by reconstruction 29, the image comprising a soft tissue image 31, a vessel image 32 and a bone image 33. By segmenting 34 a bone partial image 35 is then formed from the volume image and this substantially corresponds to the bone image in volume image 30. The bone partial image 35 is then subjected to a reprojection 36 which produces a mass occupancy partial image 37. The values of the mass occupancy partial image 37 are transformed by a subsequent transformation 38 into partial projected images and these are removed from the captured projected images 28, so, with respect to the fraction of the partial bone image 35, corrected projected images 39 result. Finally mass occupancy partial images 41 of the vessel 25 and the soft tissue 24 are created by an inversion 40, on the basis of which images renewed reconstruction 42 can be carried out which comprises an improved soft tissue image 43 and an improved vessel image 44. It should be noted that the soft tissue image 43 and the vessel image 44 may still contain remnants 45 and 46 of the bone image 33.

The remnants 45 and 46 can be reduced further by the second method stage shown in FIG. 5. The method steps shown in FIG. 5 correspond in this case to steps 1 to 6 which are described in section 4.2.1.

According to FIG. 5. a corrected soft tissue image 48 can firstly be created by segmenting 47 the soft tissue image 43 and a corrected vessel image 50 by segmenting 49 the vessel image 44. The corrected soft tissue image 48 and the corrected vessel image 50 can then each be subjected to reprojections 51 and 52 that lead to mass occupancy partial images 53. A search 54 for a mass occupancy partial image 55 of the bone 26 can then be carried out on the basis of mass occupancy partial images 53, in the course of which the mass occupancy for the bone material is sought which minimizes the difference in the projected images associated with the mass occupancy partial images 53 and the mass occupancy partial image 55 of the bone in the different energy fields from the captured projected images 28. This results in a mass occupancy partial image 55 of the bone 26 from which an improved bone image 57 results by reconstruction 56.

The improved mass occupancy partial image 55 can finally be subjected to the transformation 38 shown in FIG. 4 and thus contribute to the further improvement of the soft tissue image 43 and the vessel image 44 in an additional method stage. The method stage shown in FIG. 5 can then be started afresh. The two method stages shown in FIGS. 4 and 5 can be repeated until the remnants 45 and 46 are negligible.

FIGS. 6 and 7 show a further exemplary embodiment in which the soft tissue 24 is treated as the first material and bone 26 as the second material while the third material is the contrast medium-filled vessel 25.

Segmenting 34 in the first method stage shown in FIG. 6 accordingly provides a vessel partial image 58 which following the application of reprojection 36, transformation 38, inversion 40 and reconstruction 42 becomes a material-selective soft tissue image 59 and a material-selective bone image 60 which may each contain remnants 61 and 62 of the vessel partial image 58.

Starting from the soft tissue image 59 and the bone image 60 a corrected soft tissue image 63 and a corrected bone image 64 can be created by segmenting operations 47 and 49 in the second method stage shown in FIG. 7 and by applying reprojections 51 and 52, search 54 and reconstruction 56 a material-selective vessel image 65 can be created.

As the method steps depicted in FIGS. 4 and 5 show, the method steps shown in FIGS. 6 and 7 can also be iterated to improve accuracy.

In addition it is also possible to treat the soft tissue 24 as the third material and to separate it from the bone 26 and vessel 25.

5.2 Variants of the Iterative Chains Passed Through

The type of iterations may also be varied.

In the simplest form of the method only the basic method described in section 4.1 and illustrated in FIGS. 4 and 6 is carried out.

In a first expansion stage the first iterative partial cycle described in section 4.2.1 and illustrated in FIGS. 5 and 7 can additionally be carried out.

In a further expansion stage the second iterative partial cycle described in section 4.2.2 can additionally be carried out.

This long iterative cycle containing two iterative partial cycles can be carried out once or several times in succession.

5.3 Generalization to More Than Three Materials

In the case of more than three radiologically different materials it must be assumed that at least two materials can be separated by segmenting following a first CT reconstruction.

As a rule generalization of the problem-solving approach to more than three materials assumes that the homogeneity condition is met for the additional two materials. In this regard the two additional materials should have constant densities and constant attenuation coefficients.

When considering a fourth material the derivation of the theory in 2.2 should be generalized such that the functions in formulae (#4) to (#9) depend on two parameters $b_3$, $b_4$ instead of one $b_3$.

In the basic method in section 4.1 segmenting in step 2 and reprojection in step 3 should be carried out for the third and fourth materials. Steps 4 to 6 should be generalized to two parameters accordingly since the dependencies of the third and fourth materials should now be taken into account.

6. Advantages of the Proposed Problem-Solving Method

In contrast to the previous prior art, with knowledge of the CT-reconstructed distribution of two materials it is possible to quantitively correctly reconstruct the density distribution of even a third material and possibly even more materials in an additional iterative step.

The accuracy of material-separation may be increased by applying the iterative cycles described here.

The problem-solving method automatically implies beam hardening correction. What is described in CT technical literature as water correction or bone correction is no longer required.

Owing to the implicit elimination of artifacts the reconstructed images do not contain any of the typical hardening artifacts, such as "cupping" or dark bands between bones.

Finally reference should be made to the fact that features and properties which have been described in connection with a specific exemplary embodiment can also be combined with a different exemplary embodiment except for when this is ruled out for reasons of compatibility.

Reference is also made to the fact that in the claims and description the singular includes the plural except for when something else emerges from the context. Both the singular and the plural are meant in particular when the indefinite article is used.

The invention claimed is:

1. A method for creating material-selective volume images, comprising:
generating radiation in different energy fields using a radiation source;
x-raying an object, composed of various material components, in different energy fields and from different directions of projection;
loading a detector with the radiation and capturing projected images in different energy fields by way of the detector device;
creating material-selective volume images via an evaluation unit connected downstream of the detector;
creating a volume image of the object using a series of projected images captured from different directions of projection;
segmenting a volume image of at least one secondary component out of the volume image in addition to a number of main components, which corresponds to at most the number of energy fields;
creating mass occupancy partial images linked to the at least one secondary component in the different energy fields by back projection of the volume image of the at least one secondary component in the different energy fields;
producing corrected projected images in different energy fields from the captured projected images by removing fractions corresponding to the mass occupancy partial images;
creating mass occupancy partial images of the main components using the corrected projected images by inversion of a multi-dimensional attenuation function; and
creating material-selective volume images of the main components using the mass occupancy partial images.

2. The method as claimed in claim 1, wherein
the material-selective volume images of the main components are segmented into corrected volume images of the main components and the remnants of the at least one secondary component, wherein
corrected mass occupancy partial images of the main components are created by reprojection of the corrected volume images of the main component, wherein
a corrected mass occupancy partial image of the at least one secondary component is sought in the different energy fields pertaining to the various directions of projection, the corrected mass occupancy partial image minimizing the difference in the projected images associated with the corrected mass occupancy partial images of the main components and with the mass occupancy partial image of the at least one secondary component in the different energy fields from the captured projected images.

3. The method as claimed in claim 2, wherein a material-selective volume image of the at least one secondary component is created from the mass occupancy partial image of the at least one secondary component.

4. The method as claimed in claim 3, wherein by removing fractions corresponding to the corrected mass occupancy partial images corrected projected images are produced in different energy fields from the captured projected images, wherein
mass occupancy images of the main components are created using the corrected projected images by inversion of a multi-dimensional attenuation function, and wherein
material-selective volume images of the main components are created using the mass occupancy images.

5. The method as claimed in claim 4, wherein a plurality of method steps are iteratively repeated.

6. The method as claimed in claim 2, wherein by removing fractions corresponding to the corrected mass occupancy partial images corrected projected images are produced in different energy fields from the captured projected images, wherein
mass occupancy images of the main components are created using the corrected projected images by inversion of a multi-dimensional attenuation function, and wherein material-selective volume images of the main components are created using the mass occupancy images.

7. The method as claimed in claim 2, wherein the mass occupancy partial image of the at least one secondary component is transformed into partial projected images in the different energy fields using the multi-dimensional attenuation function.

8. The method as claimed in claim 7, wherein pre-calculated tabular values that are stored in a memory are used for the attenuation function.

9. The method as claimed in claims 2, wherein the corrected projected images are created by subtracting the partial projected images associated with the mass occupancy partial images from the captured projected images.

10. The method as claimed in claim 2, wherein pre-calculated tabular values that are stored in a memory are used for inversion of the attenuation function.

11. The method as claimed in claim 2, wherein pre-calculated tabular values that are stored in a memory are used for reprojection of the volume images of the main component and the at least one secondary component.

12. The method as claimed in claim 1, wherein the mass occupancy partial image of the at least one secondary component is transformed into partial projected images in the different energy fields using the multi-dimensional attenuation function.

13. The method as claimed in claim 12, wherein pre-calculated tabular values that are stored in a memory are used for the attenuation function.

14. The method as claimed in claims 1, wherein the corrected projected images are created by subtracting the partial projected images associated with the mass occupancy partial images from the captured projected images.

15. The method as claimed in claim 1, wherein pre-calculated tabular values that are stored in a memory are used for inversion of the attenuation function.

16. The method as claimed in claim 1, wherein pre-calculated tabular values that are stored in a memory are used for reprojection of the volume images of the main component and the at least one secondary component.

17. The method as claimed in claim 1, wherein the main components and the secondary components are selected from the group of material components consisting of bone tissue, soft tissue, tissue enriched with contrast medium, and implants.

18. The method as claimed in claim 1, wherein the main components are soft tissue with contrast medium and soft tissue without contrast medium and the secondary component is bone tissue.

19. The method as claimed in claim 1, wherein the main components are bone tissue and soft tissue without contrast medium and the secondary component is soft tissue enriched with contrast medium.

* * * * *